United States Patent [19]

O'Reilly et al.

[11] Patent Number: 4,981,999
[45] Date of Patent: Jan. 1, 1991

[54] SELECTIVE REMOVAL OF CHLORINE FROM CHLOROPHTHALIC COMPOUNDS

[75] Inventors: Neil J. O'Reilly, Grand Island; William S. Derwin, Buffalo; Henry C. Lin, Grand Island, all of N.Y.

[73] Assignee: Occidental Chemical Corporation, Niagara Falls, N.Y.

[21] Appl. No.: 439,227

[22] Filed: Nov. 20, 1989

[51] Int. Cl.$^5$ .................. C07C 51/083; C07C 51/377
[52] U.S. Cl. .................... 562/480; 502/324; 502/325; 502/340; 502/343; 502/345; 502/355; 560/83
[58] Field of Search ............................ 562/480; 560/80

[56] References Cited

U.S. PATENT DOCUMENTS 4,302,396 11/1981 Tsujimoto et al. ............. 562/480 X
4,684,737 8/1987 Horino et al. ........................ 549/240

FOREIGN PATENT DOCUMENTS 2751173 5/1979 Fed. Rep. of Germany .
64-52737 2/1989 Japan .

OTHER PUBLICATIONS

Tashiro et al., vol. 42, No. 5, pp. 835–839, (1977), J. Org. Chem.
Deacon et al., Tetrahedron Letters, vol. 25, No. 7, pp. 783–784, (1984).

Primary Examiner—Werren B. Lone
Assistant Examiner—Vera C. Clarke
Attorney, Agent, or Firm—James F. Tao; Richard D. Fuerle

[57] ABSTRACT

Disclosed is a method of selectively removing chlorine atoms in the order of fifth position first, fourth position second, and third position third from a chlorophthalic compound having at least two ring chlorine atoms such as a chlorophthalic acid or a chlorophthalic anhydride. The chlorophthalic compound is reacted in solution with a hydrodechlorinating metal in the presence of a base.

22 Claims, No Drawings

SELECTIVE REMOVAL OF CHLORINE FROM CHLOROPHTHALIC COMPOUNDS

BACKGROUND OF INVENTION

This invention relates to a method for selectively removing chlorine atoms from chlorophthalic compounds. In particular, it relates to the removal of the chlorine atoms in the order of fifth position first, fourth position second, and third position third, by reacting the chlorophthalic compound in a solution with a hydrodechlorinating metal in the presence of a base.

One route to the preparation of quinolone antibacterials involves the use of 2,4,5-trifluorobenzoic acid. Current methods of preparing 2,4,5-trifluorobenzoic acid are lengthy and expensive. A shorter, more direct route to the preparation of 2,4,5-trifluorobenzoic acid would be very desirable and would lower the cost of producing quinolone antibacterials, as well as many related compounds.

SUMMARY OF INVENTION

We have discovered a novel method of preparing chlorophthalic acids from which 2,4,5-trifluorobenzoic acid can be prepared by a direct and inexpensive route. The chlorophthalic acids prepared by the method of this invention are made by selectively removing chlorine atoms from chlorophthalic compounds such as chlorophthalic acids or chlorophthalic anhydrides. We have found that when a chlorophthalic compound is reacted with a hydrodechlorinating metal in the presence of a base, the ring chlorine atoms are removed in a particular order. The selective removal of the chlorine atoms permits the production of chlorophthalic acids having chlorine atoms in particular positions on the aromatic ring. The chlorine atoms can subsequently be replaced by fluorine atoms. As a result, compounds that require chlorine or fluorine atoms in particular positions on the aromatic ring which could not be easily prepared by other methods, can be prepared by the method of this invention.

DESCRIPTION OF THE INVENTION

This invention involves the selective removal of chlorine atoms from a chlorophthalic compound. Chlorophthalic compounds which can be used in the process of this invention include those having 2, 3, or 4 aromatic ring chlorine atoms. Other non-interfering substitutions, such as other halogens or alkyl groups, may also be present on the aromatic ring, although preferably they are not present. The chlorophthalic compound can be a chlorophthalic acid, a mono- or di-salt of the acid, a chlorophthalic anhydride, a compound that forms a salt of a chlorophthalic acid under the reaction conditions, such as an ester of a chlorophthalic acid, or various combinations of these compounds. While we do not wish to be bound by any theories, we believe that it is the di-salt that reacts, and therefore any compound that forms the di-salt of a chlorophthalic acid under the reaction conditions can be used. Preferred di-salts of chlorophthalic acids can be described by the general formula:

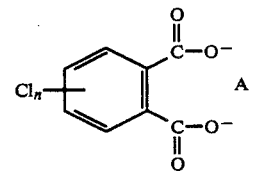

where "n" is 2, 3, or 4 and "A" is one or more cations. When "n" is 2, the two chlorines are preferably in the 3,4- 3,5-, or 3,6-position, which results in the formation of 3-chlorophthalic acid, or the 4,5-position, which results in the formation of 4-chlorophthalic acid. These acids are valuable intermediate materials because 3-chlorophthalic acid is useful in making agricultural chemicals, and 4-chlorophthalic acid is useful in making oxydiphthalic anhydride, which is used to make polyimides. When "n" is 3, the three chlorine atoms are preferably in the 3,4,6 position, because this results in the production of 3,6-dichlorophthalic acid which is useful in making herbicides. When "n" is 4, 3,4,6-trichlorophthalic acid can be produced, which can be fluorinated to produce 3,4,6-trifluorophthalic acid (see copending application Serial No. 07/315,746, filed Feb. 27, 1989 by Nowak et al., herein incorporated by reference), then decarboxylated to produce 2,4,5-trifluorobenzoic acid (see copending application Ser. No. 439,230, filed of even date by the same inventors, now U.S. Pat. No. 4,935,541, herein incorporated by reference.)

A solution of the chlorophthalic compound is made in a suitable solvent. The preferred solvent is water as it is inexpensive and has been found to work very well in the process of this invention. However, solutions in non-aqueous solvents such as methanol, ethanol, isopropanol, dimethyl sulfoxide, acetonitrile, and the like may also be suitable. The concentration of chlorophthalic compound in the solvent is not particularly important and concentrations of 1% or lower up to saturation can be used; the preferred concentration, however, is about 5 to about 20% by weight.

In the process of this invention, the chlorophthalic compound is reacted with a hydrodechlorinating metal. The hydrodechlorinating metal is a metal which, in the presence of a hydrogen source, will replace chlorine atoms on an aromatic ring with hydrogen atoms. Examples of such metals include manganese, cadmium, iron, copper, aluminum, and zinc. Zinc is preferred as it is inexpensive and works very well. While these metals normally replace chlorine atoms indiscriminately, so that the proportion of the different isomers produced is approximately equal, we have found that in the process of this invention hydrodechlorinating metals selectively remove chlorine atoms from the aromatic ring. The chlorine atoms in the fifth position are removed first, followed by chlorine atoms in the fourth position, then by chlorine atoms in the third position. As a result, the proportion of the isomers produced is not equal and typically the reaction conditions can be controlled so that over 90% of the product will be a single isomer that is in accord with this selection. The amount of hydrodechlorinating metal that is present should be at least stoichiometric. For example, one-half mole of zinc is required for the removal of each mole of chlorine. However, because the hydrodechlorinating metal can be used up in side reactions, it is preferable to have an excess of up to about 6 equivalents of the hydrodechlorinating metal present. Of course, the hydrodechlorinating metal is preferably present in a finely divided form to maximize its surface area and, therefore, the rate of reaction.

The reaction proceeds in the presence of a base such as sodium hydroxide or potassium hydroxide or other alkali. Sodium hydroxide and potassium hydroxide are preferred, as they are inexpensive and very effective. The concentration of alkali affects the number of chlorines that are removed, but concentrations from 1% or lower up to saturation may be used. If a single chlorine atom is to be removed, the preferred concentration alkali is about 1 to about 10% by weight, and, if two or more chlorine atoms are to be removed, the preferred concentration is about 10 to about 20% by weight. If the solvent is water, the pH should be greater than 7 and preferably greater than 10. The reaction will proceed at a temperature of room temperature or lower to reflux.

The product of the reaction is a chlorophthalic acid salt having one or more fewer ring chlorine atoms than did the starting chlorophthalic compound. The number of chlorines that are removed depends upon the time of reaction, the temperature, and the concentration of the base that is present, and these parameters can be controlled to remove only the desired number of chlorine atoms.

As an optional additional last step, the solution containing the chlorophthalic acid salt can be acidified, which results in the precipitation of the salt of the chlorophthalic acid. For example, when the base is sodium hydroxide, the disodium salt of the chlorophthalic acid precipitates. The precipitation of the salt of the acid is surprising since one would normally expect the acid itself to precipitate.

To form the chlorophthalic acid from the salt, the salt is collected and acidified in the presence of a solvent that dissolves the acid but not the salt, or that dissolves the salt but not the acid. For example, ethyl acetate will dissolve the acid, but will not dissolve the sodium salt.

The following examples further illustrate this invention.

EXAMPLE 1

Preparation of 3,4,6-Trichloroohthalic Acid from Tetrachlorophthalic Anhydride

A 12 liter, round-bottom, 3-neck flask equipped with a mechanical stirrer, a thermometer, and a condenser, was charged under a nitrogen atmosphere with 7500 mL of 5% aqueous caustic (375.2 g NaOH) and 750 grams of tetrachlorophthalic anhydride (purchased from Aldrich Chemical Co.). To the stirred reaction mixture was added 525 grams of zinc dust over a 5 minute period. The reaction mixture was then heated to 60° C. and stirred at that temperature for 4 hours.

After cooling to room temperature, the reaction mixture was filtered and the filter cake was washed with 2×200 mL of 0.1 N aq. NaOH followed by 2×200 mL of water. The filtrate was acidified to pH 0.9–1.0 by the careful addition of conc. hydrochloric acid with good stirring, and the product (the disodium salt) was then collected and washed with 3×100 mL of 0.1 N aq. HCl. The filtrate was put aside.

The product salt (still damp) was then slurried with 4 L of ethyl acetate and acidified with conc. HCl until all the solids had dissolved. The resulting layers were separated and the aqueous layer was extracted with 2×200 mL of ethyl acetate, and the combined organic extracts were dried over anhydrous magnesium sulfate. The solution was filtered, the solvent was removed on a rotary evaporator ahd the product was then dried in a vacuum desiccator (80–90° C., 0.5 mmHg 32 h) to give 3,4,6-trichlorophthalic acid [598.4 g, 84.7% yield, 97.8% purity by gas chromatography (gc)], mp 150–153° C.

Extraction of the filtrate with 4×750 mL of ethyl acetate, followed by drying with magnesium sulfate, filtration, and evaporation of the solvent on a rotary evaporator gave a further 44.8 g of product (6.3 % yield, 57.6 % purity by gc).

EXAMPLE 2

Isolation of 3,4,6-Trichloroohthalic Acid, Disodium Salt

A portion of the disodium salt from the above reaction was isolated by further drying in a vacuum desiccator overnight to give 3,4,6-trichlorophthalic acid, disodium salt; mp >340° C.

EXAMPLE 3

Preparation of 3,6-Dichloroohthalic Acid by Hvdrodechlorination of Tetrachlnrophthalic Anhydride A 25 mL round-bottom flask equipped with a condenser and a magnetic stirrer was charged with 1.02 g of tetrachlorophthalic anhydride, 0.71 g of zinc dust, and 10 mL of 20% (w/w) aqueous NaOH. The reaction mixture was then heated at a bath temperature of 98–103° C. with stirring for 26.5 h. The reaction mixture was then filtered, acidified with hydrochloric acid and extracted with ethyl acetate. The extract was shown to contain 53% 3,6-dichlorophthalic acid by gc analysis. The retention time was identical to that of an authentic sample.

EXAMPLE 4

Preparation of 3,4,6-Dichloroohthalic Acid by Hydrodechlorination of 3 4,6-Trichloroohthalic Acid A 25 mL round-bottom flask equipped with a condenser and a magnetic stirrer was charged with 1.01 g of 3,4,6-trichlorophthalic acid, 1.4 g of zinc dust, and 10 mL of 10% (w/w) aqueous NaOH. The reaction mixture was then heated at a bath temperature of 98–102° C. with stirring for 48.3 h. The reaction mixture was then filtered, acidified with hydrochloric acid and extracted with ethyl acetate. The extract was shown to contain 69.8% 3,6-dichlorophthalic acid by gc analysis. The retention time was identical to that of an authentic sample.

EXAMPLE 5

Preparation of 3-Chlorophthalic Acid by Hydrodechlorination of 3,4,6-Trichlorophthalic Acid A 25 mL round-bottom flask equipped with a condenser and a magnetic stirrer was charged with 1.00 g of 3,4,6-trichlorophthalic acid, 1.4 g of zinc dust, and 10 mL of 20% (w/w) aqueous NaOH. The reaction mixture was then heated at a bath temperature of 100–103° C. with stirring for 64.7 h. The reaction mixture was then filtered, acidified with hydrochloric acid and extracted with ethyl acetate. The extract was shown to contain 59.7% 3-chlorophthalic acid by gc analysis. The retention time was identical to that of an authentic sample.

EXAMPLE 6

Preparation of 4-Chlorophthalic Acid from 4,5-Dichlorophthalic Anhydride

A 10 mL flask equipped with a condenser and a magnetic stirrer was chagged with 0.2 g 4,5-dichlorophthalic anhydride, 0.28 g of zinc dust, and 2 mL of 10% aq. NaOH. The reaction mixture was heated with stirring at a bath temperature of 93–108° C. for 8.7 h. The reaction mixture was then acidified with hydrochloric acid and extracted with ethyl acetate. Analysis of the extract indicated a 95% yield (gc area%) of 4-chlorophthalic acid, at 86% conversion. The retention time of the peak was identical with that of an authentic sample.

EXAMPLE 7

Examples 7 to 10 are comparative examples. Example 1 was repeated except that Raney-nickel in 25% aqueous KOH was used instead of zinc and NaOH. The product was 93% phthalic acid and 6% tetrahydrophthalic acid. A less active form of nickel, however, may remove less than all of the chlorines.

EXAMPLE 8

Example 1 was repeated except that ethanol/aqueous HCl was used instead of 5% aqueous caustic. The result was only an 18% yield (36% conversion) after 43 h at 88–100° C. This example shows that the presence of a base is necessary.

EXAMPLE 9

Example 1 was repeated using tetrabromophthalic anhydride with 72 wt % zinc and 20% aqueous NaOH. After one hour at 60° C., 97% phthalic acid was produced. This example shows that the process of this invention is ineffective in selectively removing bromine.

EXAMPLE 10

Example 1 was repeated except that tetrafluorophthalic acid and 20% sodium hydroxide were used. A gc analysis showed that the products were about 59% by weight 4-hydroxy-3,5,6-trifluorophthalic acid, about 37% 2-hydroxy-1,3,4-trifluorobenzoic acid, and only about 3% 3,4,6-trifluorophthalic acid. This example shows that the process of this invention is ineffective in selectively hydrodefluorinating fluorophthalic acids in good yields.

We claim:

1. A method of selectively removing chlorine atoms in the order fifth position first, fourth position second, and third position third, from a chlorophthalic compound having at least two ring chlorine atoms, comprising forming a solution of said chlorophthalic compound and reacting said chlorophthalic compound in said solution with a hydrodechlorinating metal in the presence of a base, whereby a partially dechlorinated chlorophthalic acid is formed.

2. A method according to claim 1 wherein said solution is heated to a temperature between room temperature and reflux.

3. A method according to claim 1 wherein said hydrodechlorinating metal is zinc.

4. A method according to claim 1 wherein said base is NaOH or KOH.

5. A method according to claim 1 wherein said chlorophthalic compound has the formula

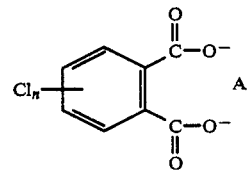

where "n" is 2 to 4, and A is cation.

6. A method according to claim 1 wherein said chlorophthalic compound is selected from the group consisting of 3,4-dichlorophthalic anhydride, 3,5-dichlorophthalic anhydride, 4,5-dichlorophthalic anhydride, and mixtures thereof.

7. A method according to claim 1 wherein said chlorophthalic compound is a chlorophthalic acid.

8. A method according to claim 7 wherein said chlorophthalic acid is 3,4,6-trichlorophthalic acid.

9. A method according to claim 1 wherein said chlorophthalic compound is tetrachlorophthalic anhydride.

10. A method according to claim 1 including the additional last step of acidifying said solution to precipitate the salt of said partially dechlorinated chlorophthalic acid.

11. A method according to claim 10 wherein said base is sodium hydroxide and said salt is the disodium salt.

12. A method according to claim 10 including the additional last step of acidifying said salt in the presence of a solvent in which only one of said dechlorinated chlorophthalic acid and its salt is soluble.

13. A method of making 4-chlorophthalic acid comprising heating an aqueous alkaline solution of 4,5-dichlorophthalic anhydride to a temperature between room temperature and reflux in the presence of a hydrodechlorinating metal.

14. A method according to claim 13 wherein said hydrodechlorinating metal is zinc.

15. A method of making 3-chlorophthalic acid comprising heating an aqueous alkaline solution of a chlorophthalic compound selected from the group consisting of 3,4-dichlorophthalic anhydride, 3,5-dichlorophthalic anhydride, 3,6-dichlorophthalic anhydride, and mixtures thereof to a temperature between room temperature and reflux in the presence of a hydrodechlorinating metal.

16. A method according to claim 15 wherein said hydrodechlorinating metal is zinc.

17. A method of selectively removing one, two, or three chlorine atoms from tetrachlorophthalic anhydride, in the order: fifth position, then the fourth position, then the third position, comprising
   (A) forming an aqueous alkaline solution of said tetrachlorophthalic anhydride in the presence of a hydrodechlorinating metal; and
   (B) heating said solution to a temperature between room temperature and reflux 18. A method according to claim 17 wherein said hydrodechlorinating metal is zinc.

19. A method according to claim 17 wherein a single chlorine atom is removed, forming 3,4,6-trichlorophthalic acid.

20. A method according to claim 17 wherein two chlorine atoms are removed, forming 3,6-dichlorophthalic acid.

21. A method according to claim 17 wherein three chlorine atoms are removed, forming 3-chlorophthalic acid.

22. A method according to claim 1 wherein said reacting is at room temperature.

* * * * *